US009222351B2

(12) United States Patent
Jamison

(10) Patent No.: US 9,222,351 B2
(45) Date of Patent: Dec. 29, 2015

(54) SYSTEMS AND METHODS FOR REAL-TIME SAG DETECTION

(71) Applicant: Dale E. Jamison, Houston, TX (US)

(72) Inventor: Dale E. Jamison, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 211 days.

(21) Appl. No.: 13/713,447

(22) Filed: Dec. 13, 2012

(65) Prior Publication Data
US 2014/0172305 A1 Jun. 19, 2014

(51) Int. Cl.
E21B 44/00 (2006.01)
E21B 21/00 (2006.01)
E21B 47/09 (2012.01)
E21B 47/10 (2012.01)
E21B 49/00 (2006.01)
G01N 15/04 (2006.01)
E21B 21/08 (2006.01)
G01N 9/26 (2006.01)
G01N 9/36 (2006.01)

(52) U.S. Cl.
CPC ............ *E21B 47/0905* (2013.01); *E21B 21/08* (2013.01); *E21B 44/00* (2013.01); *E21B 47/10* (2013.01); *E21B 49/005* (2013.01); *G01N 15/04* (2013.01); *G01N 9/26* (2013.01); *G01N 9/36* (2013.01)

(58) Field of Classification Search
CPC ....... E21B 44/00; E21B 44/08; E21B 48/008; E21B 48/087; E21E 49/008; E21E 49/087; G01V 3/00
USPC .................................................... 702/9; 70/9
See application file for complete search history.

(56) References Cited

U.S. PATENT DOCUMENTS

| 5,083,622 | A | 1/1992 | Hale et al. | |
| 5,085,282 | A | 2/1992 | Hale et al. | |
| 6,176,323 | B1* | 1/2001 | Weirich et al. | 175/40 |
| 6,198,531 | B1 | 3/2001 | Myrick et al. | |
| 6,330,826 | B1* | 12/2001 | Meeten | 73/152.62 |

(Continued)

FOREIGN PATENT DOCUMENTS

EP 1048819 A1 11/2000
WO 2011124978 A2 10/2011

(Continued)

OTHER PUBLICATIONS

Skalle et al., Barite Segregation in Inclined Boreholes, 1999, Journal of Canadian Petroleum Technology, Special Edition 1999, vol. 38, No. 13, pp. 1-6.*

(Continued)

*Primary Examiner* — Gregory J Toatley
*Assistant Examiner* — Michael Dalbo
(74) *Attorney, Agent, or Firm* — McDermott Will & Emery LLP; Scott Brown

(57) ABSTRACT

Disclosed are systems and methods for the real-time detection and measurement of sag within a deviated borehole. One method includes measuring a first pressure at a first time at a point within the borehole, predicting a characteristic of the drilling fluid at the point using a computer model, thereby obtaining a predicted characteristic, calculating the characteristic based on the first pressure, thereby obtaining a calculated characteristic, and determining whether sag has occurred based on a comparison between the calculated characteristic and the predicted characteristic.

14 Claims, 7 Drawing Sheets

(56) References Cited

U.S. PATENT DOCUMENTS

| | | |
|---|---|---|
| 6,529,276 B1 | 3/2003 | Myrick |
| 6,584,833 B1 | 7/2003 | Jamison et al. |
| 6,585,044 B2 | 7/2003 | Rester et al. |
| 7,123,844 B2 | 10/2006 | Myrick |
| 7,834,999 B2 | 11/2010 | Myrick et al. |
| 7,911,605 B2 | 3/2011 | Myrick et al. |
| 7,920,258 B2 | 4/2011 | Myrick et al. |
| 8,049,881 B2 | 11/2011 | Myrick et al. |
| 8,208,147 B2 | 6/2012 | Myrick et al. |
| 8,575,541 B1 | 11/2013 | Jamison et al. |
| 2001/0036905 A1 | 11/2001 | Parlar et al. |
| 2002/0010548 A1* | 1/2002 | Tare et al. ............ 702/9 |
| 2002/0071121 A1 | 6/2002 | Ortyn et al. |
| 2003/0013614 A1 | 1/2003 | Klug et al. |
| 2003/0084717 A1 | 5/2003 | Herzhaft et al. |
| 2003/0183393 A1 | 10/2003 | Fincher et al. |
| 2005/0034535 A1* | 2/2005 | Sprague ............ 73/861.22 |
| 2005/0269135 A1 | 12/2005 | Swartout |
| 2006/0142955 A1 | 6/2006 | Jones et al. |
| 2007/0138103 A1 | 6/2007 | Klatt |
| 2008/0111064 A1 | 5/2008 | Andrews et al. |
| 2008/0142211 A1 | 6/2008 | Klatt |
| 2008/0283294 A1 | 11/2008 | Colquhoun |
| 2009/0182693 A1 | 7/2009 | Fulton et al. |
| 2009/0194330 A1 | 8/2009 | Gray |
| 2009/0219539 A1 | 9/2009 | Myrick et al. |
| 2009/0219597 A1 | 9/2009 | Myrick et al. |
| 2010/0193249 A1 | 8/2010 | Saiz |
| 2011/0108720 A1 | 5/2011 | Ford et al. |
| 2011/0167901 A1 | 7/2011 | Jamison et al. |
| 2012/0046870 A1 | 2/2012 | Lievois et al. |
| 2012/0150451 A1 | 6/2012 | Skinner et al. |
| 2012/0165231 A1* | 6/2012 | Miller et al. ............ 507/143 |
| 2012/0211650 A1 | 8/2012 | Jones et al. |
| 2013/0213648 A1 | 8/2013 | Sroka et al. |
| 2014/0076551 A1 | 3/2014 | Pelletier et al. |
| 2014/0110105 A1 | 4/2014 | Jones et al. |
| 2014/0166361 A1 | 6/2014 | Jamison et al. |
| 2014/0166871 A1 | 6/2014 | Jamison et al. |
| 2014/0172177 A1 | 6/2014 | Jamison et al. |

FOREIGN PATENT DOCUMENTS

| | | |
|---|---|---|
| WO | 2014093161 A1 | 6/2014 |
| WO | 2014093167 A1 | 6/2014 |
| WO | 2014093432 A1 | 6/2014 |
| WO | 2014093572 A2 | 6/2014 |
| WO | 2014093629 A1 | 6/2014 |

OTHER PUBLICATIONS

International Search Report and Written Opinion for PCT/US2013/073572 dated Mar. 25, 2014.
International Search Report and Written Opinion for PCT/US2013/074274 dated Mar. 25, 2014.
Bern et al., "Field Monitoring of Weight-Material Sag," IN: AADE Conference and Exhibition, 2010, pp. 1-11.
International Search Report and Written Opinion for PCT/US2013/073612 dated Mar. 26, 2014.
International Search Report and Written Opinion for PCT/US2013/074680 dated Mar. 27, 2014.
International Search Report and Written Opinion for PCT/US2013/074556 dated Sep. 24, 2014.

* cited by examiner

SYSTEMS AND METHODS FOR REAL-TIME SAG DETECTION

BACKGROUND

The present invention relates to detection of sag in a drilling fluid and, in particular, to the real-time detection and measurement of sag within a deviated borehole.

While drilling a gas or oil well, a drilling fluid, i.e. mud, is typically pumped down to the drill bit during drilling operations and flowed back to the surface through the annulus defined between the drill string and the walls of the borehole. A typical drilling fluid includes a weighting material, such as barite, to increase the density of the drilling fluid and thereby assist in transporting rock chips and cuttings from the drill bit to the surface.

Settling or migration of the suspended weighting materials within the drilling fluid is commonly referred to as "sag" or "barite sag," and is a known and persistent problem in drilling operations. Turbulence in the moving fluid may tend to keep particles in suspension, but when the drilling fluid becomes static, such as while tripping the drill bit or when the circulation flow rate of the drilling fluid is relatively low, the weighting material(s) may tend to settle toward the bottom of the borehole.

When sag occurs in a borehole, i.e. "a sag event," it can cause borehole pressure problems that are typically manifested when the mud pumps are turned on after quiescent periods, or during operations such as tripping in when the fluids are periodically sheared and then circulation resumed. Problematic borehole pressure spikes may occur when the drilling fluid is pumped after a sag event. The lighter drilling fluid nearer the surface is pumped out first, leaving the borehole filled with the heavier, settled drilling fluid and the newly introduced drilling fluid that is being pumped down the drill string. As the borehole is now filled with a heavier fluid, on average, and the heavier fluid may have a greater flow resistance than the original fluid and/or higher hydrostatic pressure, the borehole pressure at depth can exceed the fracture gradient of the surrounding formation, resulting in lost circulation, formation damage and/or fracturing of the formation.

Sag is aggravated in deviated or angled boreholes due to a phenomenon called "boycott settling" or the "boycott effect." Briefly, the boycott effect occurs since suspended particles tend to settle vertically downward, creating an increased-density or heavier layer along the lower side of the angled borehole and a reduced-density or lighter layer along the upper side. Such a pressure imbalance across the longitudinal cross-section of the angled borehole will tend to circulate the lighter layer upward and the heavier layer downward, significantly increasing the rate at which the heavier particles accumulate in the lower portion of the angled borehole. Accumulations of the weighting material in the lower portion of the borehole can be difficult to re-suspend and may cause drag on rotating drill strings or impede moving tools up or down through the region of accumulated weighting material.

Historically, sag mitigation has been focused on increasing the low-end rheology such as through modifying the drilling fluid to increase the viscosity at low flow rates, or using smaller-diameter weighting materials, or both. One conventional method of monitoring a borehole for sag includes periodic measurement of the density of the returning mud to detect variations which may indicate that sag is occurring somewhere within the borehole. Another conventional method is to monitor the standpipe pressure as fluctuations in the pressure may indicate non-uniform flow resistance within the borehole. These methods are indirect, at best, and the variations in mud density and pressure may be caused by factors unrelated to sag.

Those skilled in the art will readily recognize the importance in accurately determining the onset of sag, particularly in angled or deviated wells, which can adversely affect hydrocarbon production. In some cases, the operation of a well from a particular reservoir can be permanently degraded due to resistance or blockage by settled weighting material, making prevention essential to proper reservoir management. Accordingly, identifying a sag event before it becomes severe can prove advantageous in mitigating costly corrective action.

SUMMARY OF THE INVENTION

The present invention relates to detection of sag in a drilling fluid and, in particular, to the real-time detection and measurement of sag within a deviated borehole.

In some embodiments, a method of detecting sag in a drilling fluid within a borehole is disclosed. The method may include measuring a first pressure at a first time at a point within the borehole, predicting a characteristic of the drilling fluid at the point using a computer model, thereby obtaining a predicted characteristic, calculating the characteristic based on the first pressure, thereby obtaining a calculated characteristic, and determining whether sag has occurred based on a comparison between the calculated characteristic and the predicted characteristic.

In other embodiments, a system for detecting sag in a drilling fluid within a borehole. The system may include at least one sensor positioned within the borehole at a point, the sensor being configured to measure a characteristic of the drilling fluid at a first time and provide a measured characteristic, and a processor communicatively coupled to the at least one sensor and configured to receive the measured characteristic and predict a theoretical characteristic of the drilling fluid at the point, the processor being further configured to determine whether sag has occurred at the first time based on a comparison between the measured characteristic and the theoretical characteristic.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present invention relates to detection of sag in a drilling fluid and, in particular, to the real-time detection and measurement of sag within a deviated borehole.

Disclosed herein are systems and methods of determining the onset of weighting material settling and sag in real time as occurring in a deviated or angled borehole. Once sag has occurred, it may require normal operations to be suspended while specific sag mitigation procedures are implemented. If the sag is severe, it may be difficult to recover completely, and the long-term productivity of the well may be reduced. In a worst case, for example if the settled weighting material has formed a hard mass around the drill string, it may not be possible to recover operations and the well may be lost. The disclosed systems and methods may prove advantageous in detecting sag at a much earlier stage at which point drilling operations may be redirected or changed in order to minimize the problematic effects. In some cases, early detection of sag may allow an operator to proactively treat the borehole, such as by altering the dosing of the fluid system as a corrective step or action. The disclosed systems and methods may further provide real time feedback on the effectiveness of such corrective actions or treatments.

Figure 1:
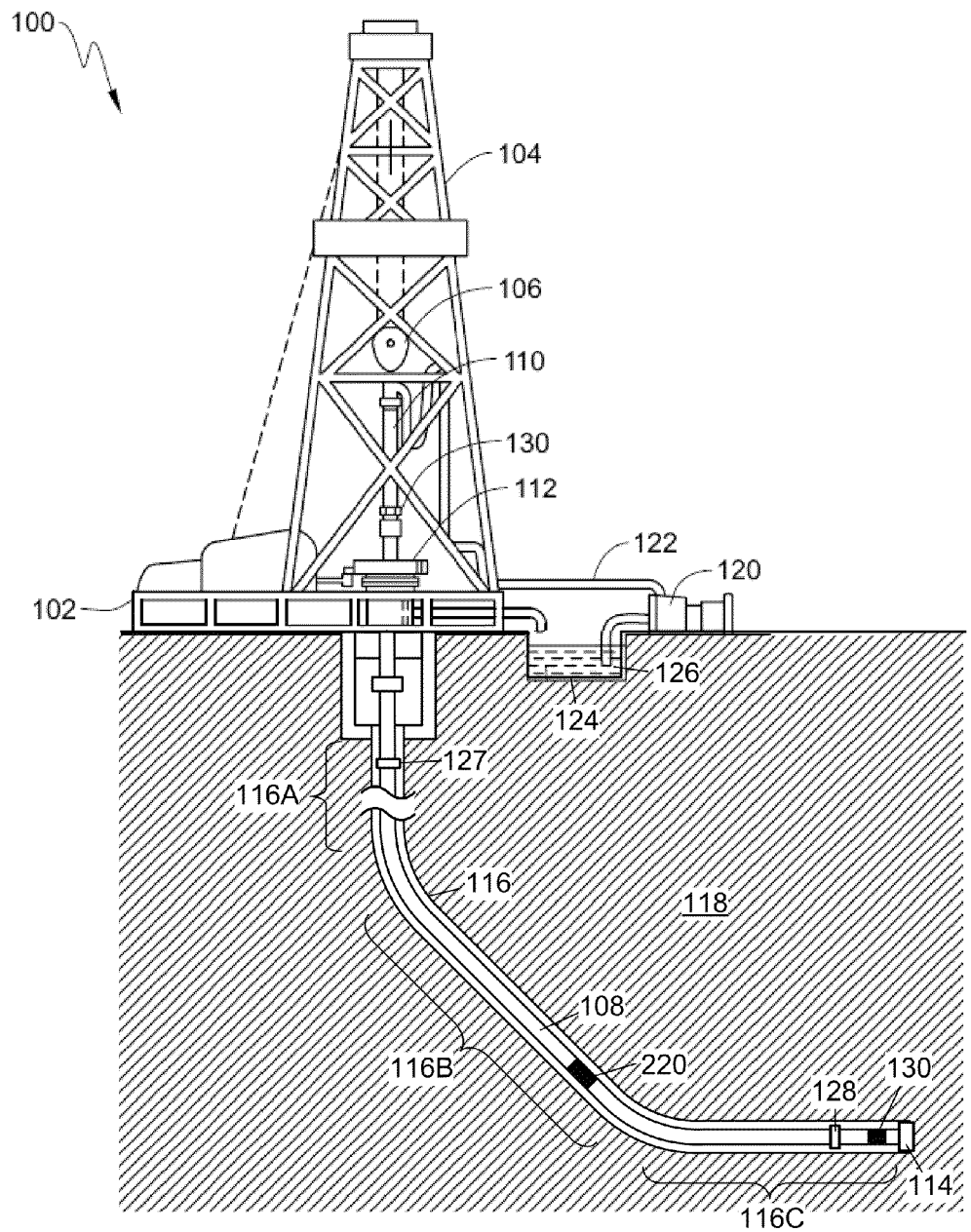
FIG. 1 illustrates a land-based oil and gas rig including one or more sensors that may be employed to detect sag, according to one or more embodiments.

FIG. 1 illustrates a land-based oil and gas rig 100 including, in this example, a downhole sag sensor 220, according to one or more embodiments. It should be noted that, even though FIG. 1 depicts a land-based oil and gas rig 100, it will be appreciated by those skilled in the art that the components of the rig 100, and various embodiments of the components disclosed herein, are equally well suited for use in other types of rigs, such as offshore platforms, or rigs used in any other geographical location.

As illustrated in FIG. 1, the rig 100 includes a drilling platform 102 that supports a derrick 104 having a traveling block 106 for raising and lowering a drill string 108. A kelly 110 supports the drill string 108 as it is lowered through a rotary table 112. The kelly 110 may be, for example, a four or six-sided pipe configured to transfer rotary motion to a turntable 130 and the drill string 108. A drill bit 114 is driven either by a downhole motor (not shown in FIG. 1) and/or via rotation of the drill string 108 from the drilling platform 102 and may include one or more drill collars 127 and 128. As the bit 114 rotates, it creates a borehole 116 that passes through various subterranean formations 118. A pump 120 circulates a drilling fluid (i.e., mud) 126 through a feed pipe 122 to the kelly 110, which conveys the drilling fluid 126 downhole through an interior conduit in the drill string 108 and through one or more orifices in the drill bit 114. The drilling fluid 126 is then circulated back to the surface via the annulus defined between the drill string 108 and the borehole 116 where it is eventually deposited in a retention pit 124. Typically, cuttings laden fluid is processed through solids control equipment such as shakers and centrifuges (not shown in FIG. 1) to remove cuttings and debris prior to being returned to retention pit 124. The drilling fluid 126 transports cuttings and debris derived from the borehole 116, aids in maintaining the integrity of the borehole 116 and provides cooling and lubrication of the drill bit 114.

The drilling fluid 126 may include at least one weighting material suspended therein or otherwise associated therewith. As known in the art, weighting materials are dense particulate materials added to drilling fluids 126 to increase the density of the drilling fluid 126, thereby assisting in carrying cuttings from the drill bit 114 to the surface as well as managing the hydrostatic pressure in the borehole 116. In one embodiment, the weighting material may be barite ($BaSO_4$), a dense sulfate mineral that naturally occurs and typically in depositional environments. In other embodiments, the weighting material may include, but is not limited to, hematite, ilmenite, manganese tetraoxide, galena, and calcium carbonate.

As illustrated in FIG. 1, the borehole 116 may be generally characterized as a deviated or angled borehole that includes various sections or portions extending at different angular directions. Specifically, the borehole 116 may include a vertical section 116A extending generally from the rig 100, an angled section 116B extending from the vertical section 116A, and a horizontal section 116C extending generally from the angled section 116C. Those skilled in the art will readily recognize that, while the angled section 116B is shown as a generally straight section of the borehole 116 with short curved sections at each end, the entire angled section 116B may be curved or otherwise exhibit one or more arcuate portions, without departing from the scope of the disclosure.

The drill string 108 may include a pressure sensor 130 disposed thereon and generally located near the drill bit 114. In some embodiments, the pressure sensor 130 may be a pressure-while-drilling (PWD) sensor. The disclosed system may also include one or more sag sensors 220 arranged along the drill string 108. The location of the sag sensors 220 are discussed in greater detail with respect to FIG. 4.

Figure 2:
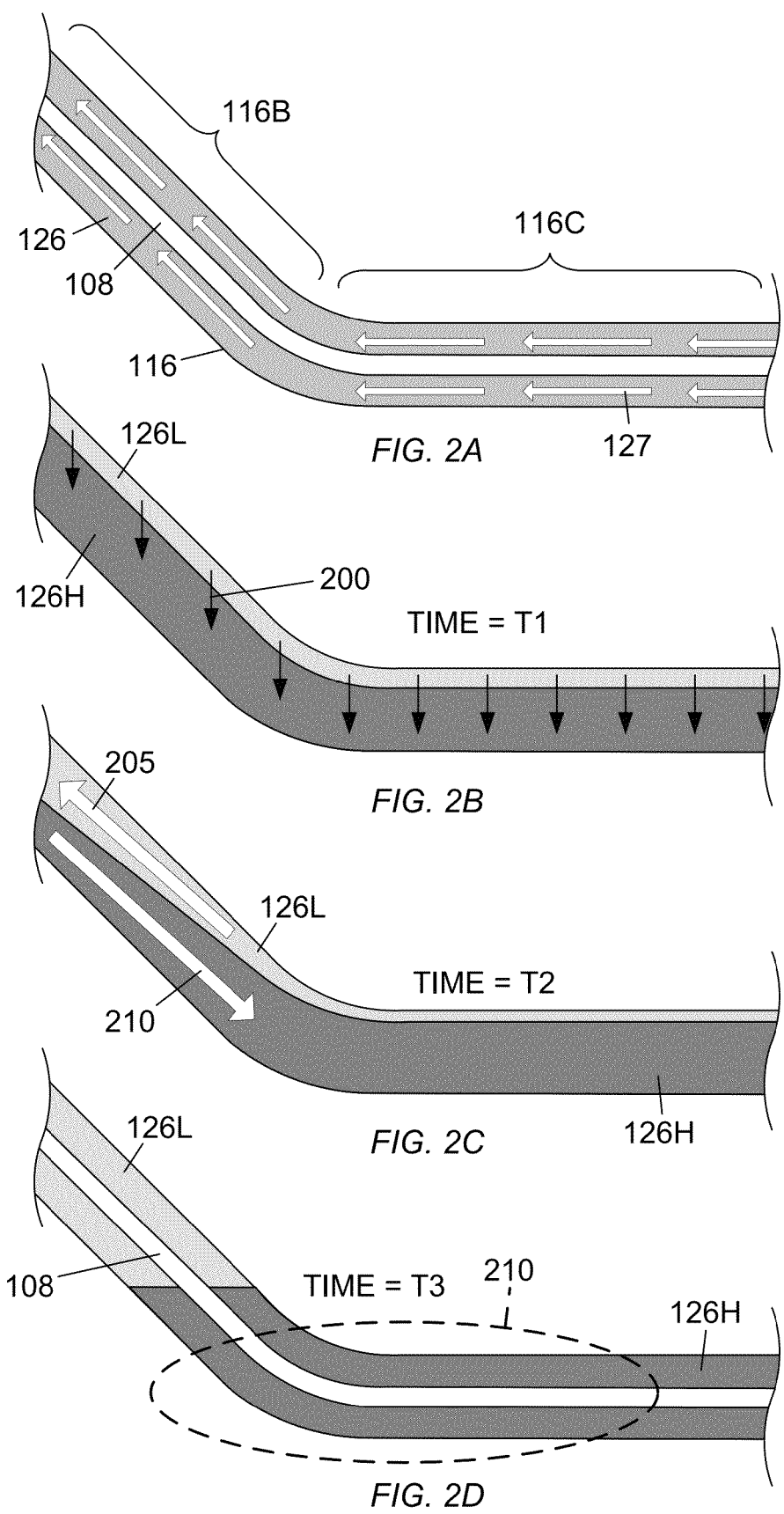
FIGS. 2A-2D depict illustrative example sequential stages of sag in an angled borehole 116, according to one or more embodiments.

Referring now to FIGS. 2A-2D, with continued reference to FIG. 1, depicted are illustrative example sequential stages of sag in the borehole 116, according to one or more embodiments. In particular, FIGS. 2A-2D generally depict the transition from the angled section 116B of the borehole 116 to the horizontal section 116C. FIG. 2A depicts normal drilling operations wherein the drill string 108 is advancing within the borehole 116 and drilling mud 126 is being returned to the surface through the annulus defined between the drill string 108 and the walls of the borehole 116, as indicated by the arrows 127. FIG. 2B is a qualitative depiction of the transition point within the borehole 116 during a period of non-operation, such as when the drilling fluid 126 ceases to circulate. As illustrated, a time T1 has passed since the cessation of drilling fluid 126 flow, and the drill string 108 has been omitted from FIG. 2B for clarity.

Once the drilling fluid 126 ceases flowing up the borehole 116, the weighting material suspended therein may start to settle within the drilling fluid 126, as generally indicated by arrows 200. After time T1 has passed, the weighting material near the upper portions of the borehole 116 may have descended or otherwise settled into the lower portions of the borehole 116, thereby starting to result in the congregation of a lighter fluid 126L near the upper side of the borehole 116 and a heavier fluid 126H near the bottom side. It can be seen that the layers of the two fluids 126L and 126H in the angled portion 116B generally follow the angle of the borehole section 116B, as the settling is vertical rather than aligned with the borehole section 116B.

As the drilling fluid 126 begins to separate into the two fluids 126L and 126H, a pressure imbalance is generated within the borehole 116 due to the differing densities of the two fluids 126L, 126H. As a result, FIG. 2C shows qualitatively how a circulating flow will form locally within the angled section 116B and the horizontal section 116C. The drill string 108 has again been omitted from FIG. 2C for clarity. The lighter fluid 126L will tend to flow upward within the angled section 116B, and thereby draw additional lighter fluid 126L from the horizontal section 116C. At the same time, the heavier fluid 126H tends to flow downward within the angled section 116B and flow into the horizontal section 116C. At a time T2 (i.e., some time after the time T1) of the configuration shown in FIG. 2B, the drilling fluid 126 will be generally distributed as shown in FIG. 2C with circulation currents within the fluids 126L and 126H as indicated by arrows 205 and 210, respectively. It can be seen that the amount of the lighter fluid 126L remaining in the horizontal section 116C is less than the amount present at time T2, shown in FIG. 2B.

FIG. 2D qualitatively shows a general distribution of the lighter and heavier fluids 126L and 126H at a time T3, after additional time has passed following the time T2 (FIG. 2C). As illustrated, the heavier fluid 126H has generally congregated and otherwise filled the horizontal section 116C and the lower portion of the angled section 116B, with the lighter fluid 126L generally congregating or otherwise filling the upper angled section 116B. At least one problem that may occur when the heavier drilling fluid 126H settles as shown in FIG. 2D is that the pump 120 (FIG. 1) may require higher pressure to initiate flow thus causing the formation to be exposed to higher and potentially destabilizing pressure. The lighter drilling fluid 126L nearer the surface is pumped out first, leaving the borehole 116 filled with the settled heavier drilling fluid 126H and the homogeneous drilling fluid 126 that is being pumped down the drill string 108. As a result, the hydrostatic pressure at the bottom of the borehole 116 can spike to a pressure that exceeds the fracture gradient of the surrounding formation 118 (FIG. 1), thereby resulting in lost circulation, formation 118 damage and/or formation 118 fracturing.

At least one additional potential problem is that the settled weighting material may cause drag on the rotating drill string 108. As accumulated weighting material in the lower portion of the borehole 116 can be difficult to re-suspend, this drag may be an ongoing issue in the operation of the rig 100.

Figure 3:
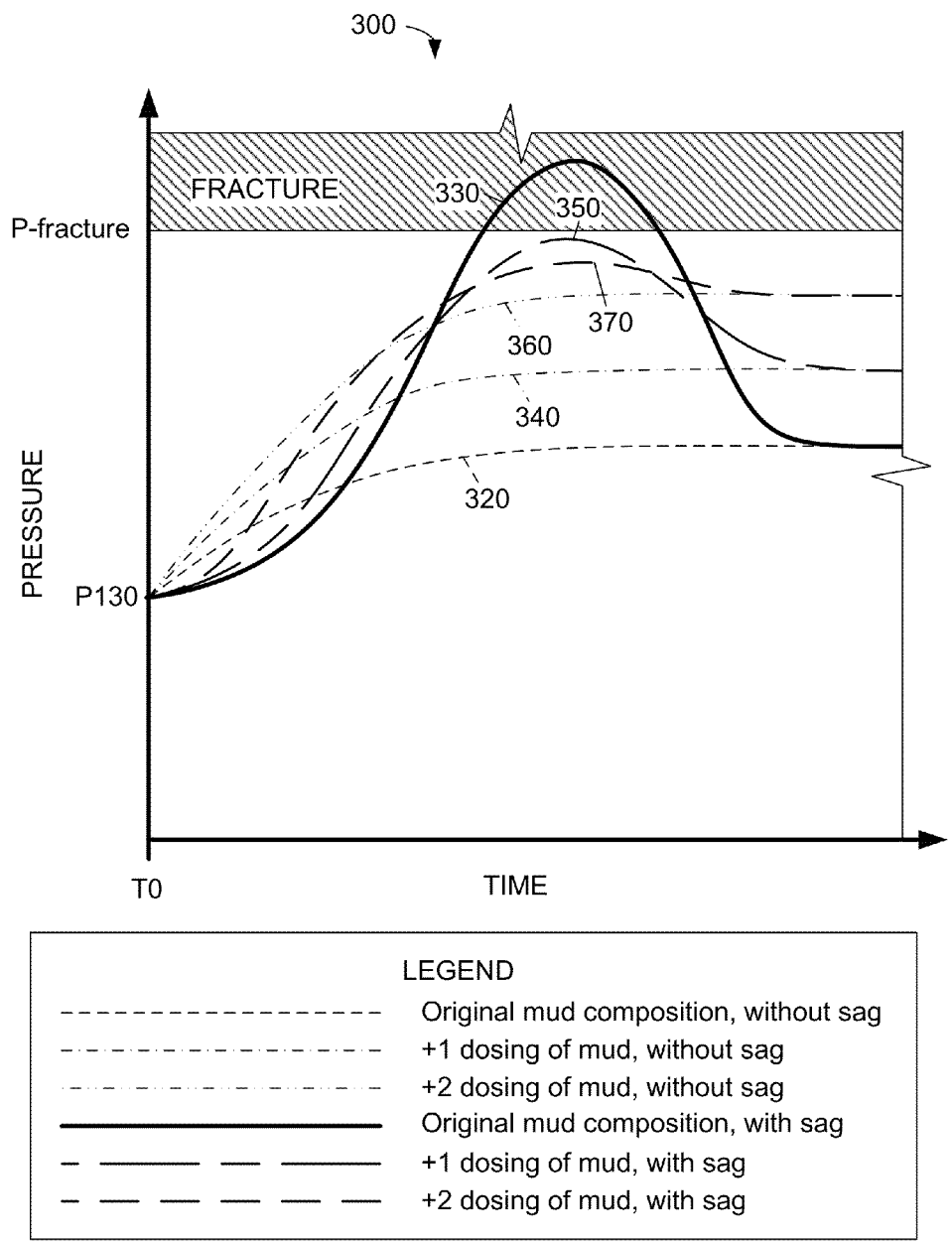
FIG. 3 is a qualitative plot of pressures near the drill bit when pumping of a drilling fluid is resumed after a quiescent period of time, according to one or more embodiments.

FIG. 3 is a qualitative plot 300 of pressure versus time at a point near the drill bit 114 (FIG. 1) when pumping of a drilling fluid 126 is resumed after a quiescent period of time, according to one or more embodiments. In this example, the pressure P130 is the dynamic pressure measured at the PWD sensor 130 (FIG. 1) for a time period starting at the resumption of pumping after a period of non-pumping. All curves are qualitative and intended for illustration only and, therefore, relative magnitudes and time relationships should not be considered as predictive of actual pressures or relationships between pressures.

Curves 320 and 330 represent the behavior of the well with a drilling fluid 126 having a baseline composition. Curve 320 is the pressure curve that would be expected if no sag has occurred, for example if the pump 120 was shut off only for a short time. The pressure will increase smoothly and asymptotically approach a stable plateau without overshoot. Curve 320 may be considered a baseline pressure curve for comparison to other pressure curves with other mud compositions and/or after sag has occurred.

Curve 330 is representative of a pressure spike that may be experienced when severe sag has occurred in the baseline drilling fluid 126. The pressure may build slower than the baseline curve 320 then rise sharply as the lighter drilling fluid 126L (FIG. 2D) is displaced from the borehole 116 by the rising heavier drilling fluid 126H, with the pressure curve 330 rising to a peak value that is greater than the fracture gradient, marked P-fracture on the vertical pressure axis, of the subterranean formation surrounding the lower end of the borehole 116. As the heavier fluid 126H is carried out of the borehole 116, the pressure curve 330 will drop to match the baseline curve 320. The damage, however, has been done and the drill rig operators are likely to face a significant amount of work to recover control of the well that may be expensive in both time and money.

Curves 340, 350, 360, and 370 qualitatively depict the expected behavior of the same borehole and quiescent period of time as curves 320 and 330 with the addition of modifiers to the drilling fluid 126. Example modifiers include, but are not limited to, thixotropic materials, clay, bentonite or other 'gels,' polymers, deflocculants, and emulsifiers. Curves 350 and 370 represent the pressures seen after circulation of the drilling fluid 126 has been stopped for the same amount of time as for curve 330.

Curves 340 and 350 describe the pressure versus time behavior for the drilling fluid 126 of curves 320, 330 to which has been added a "unit dose" of a particular modifier, which may be a blend of one or more materials. Addition of a single unit dose of the modifier, referred to herein as a "+1 dose," converts the baseline drilling fluid 126 into a drilling fluid 126A. The actual amount of a unit dose is arbitrary and intended only for comparison with curves 360, 370 that reflect the addition of two unit doses of the same modifier, referred to herein as a "+2 dose," thereby converting the baseline drilling fluid 126 into a drilling fluid 126B. Curve 340 reflects the effect of a +1 dose of the modifier in increasing the pumping resistance of the modified drilling fluid 126A and thereby increasing the plateau pressure of curve 340 compared to curve 320. The benefit of adding the modifier is seen in curve 350, where the peak pressure has been reduced, compared to curve 330, because the amount of sag that occurred in the drilling fluid 126A during the same quiescent period of time was less than the sag that occurred with the unmodified drilling fluid 126 of curve 330.

Curves 360, 370 qualitatively show the increased effect of doubling the amount of chemical modifier added to the drilling fluid 126. It should be apparent to those of skill in the art that the relative changes are illustrative only and the true effects may not be linear with the amount of added chemical modifier and are very dependent upon the type of composition of the base drilling fluid as well as the choice of chemicals that make up the chemical modifier. The addition of two unit doses of the chemical modifier can be seen to increase the pressure plateau of curve 360 in the absence of sag, as the drilling fluid 126B will have even more pumping resistance than the +1 dose drilling fluid 126A of curve 340. Curve 370 illustrates that when sag occurs in the +2 dose drilling fluid 126B, however, the peak pressure is further reduced compared to the +1 dose curve 350.

It will be apparent that the proper dosing of modifier to be added to the drilling fluid 126 is a balance between sag reduction and accepting an increase in the on-going pumping resistance. Unnecessarily adding a modifier having the effects shown in FIG. 3 may create problems with the pumping equipment due to the added pumping resistance of the modified drilling fluids 126A, 126B, or decrease the amount of suspended cutting that settle out of the drilling fluids 126A, 126B in the retention pit 124.

Figure 4:
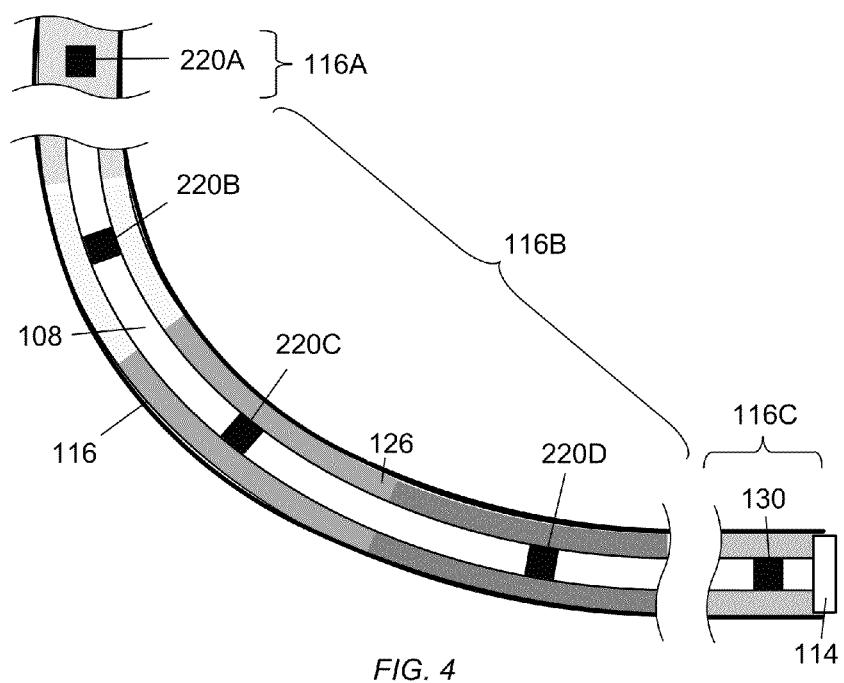
FIG. 4 is a simplified diagram of a portion of an inclined borehole showing an exemplary arrangement of distributed sensors, according to one or more embodiments.

Detection of sag in real time may enable operators to avoid unnecessarily adding modifiers to the drilling fluid 126, thereby enabling them to take corrective action only when sag occurs. Such corrective actions may include, but are not limited to, product dosing to change the settling characteristics of the fluid, fluid circulation to mix and displace the settling/sagging fluid, changing the rate of rotation of the drill string 108, changing the tripping speed and tripping with pumping. Referring now to FIG. 4, illustrated is a simplified diagram of a portion of a deviated or angled borehole 116 showing an exemplary arrangement of distributed sag sensors 220, according to one or more embodiments. In particular, FIG. 4 shows a curved section 116B between a generally vertical section 116A and a generally horizontal section 116C of the borehole 116. In this example, four sag sensors 220A, 220B, 220C, and 220D have been placed in the drill string 108 at various separated points that are distributed through the curved section 116B. A PWD sensor 130 is also visible near the drill bit 114.

The annulus defined between the drill string 108 and the walls of the borehole 116 is filled with drilling fluid 126. The shading of the fluid 126 is intended to indicate the relative density of the local drilling fluid 126, with the drilling fluid 126 having a baseline density in the regions surrounding the PWD sensor 130 and the sag sensor 220A. As illustrated, the drilling fluid 126 has partially separated within the angled section 116B, wherein the fluid surrounding sag sensor 220B may exhibit the lowest density, the drilling fluid 126 surrounding the sag sensor 220C may exhibit an intermediate density, and the drilling fluid 126 surrounding the sag sensor 220D may exhibit the highest density. Pressures at the various sensors 130, 220A-D are discussed in greater detail with respect to FIG. 5. The number of distributed sag sensors 220 may vary in various embodiments. In certain embodiments, only one sag sensor 220 may be required so long as the sag sensor 220 is positioned within the region of the sagged drilling fluid 126, either within the heavier drilling fluid 126H or the lighter drilling fluid 126L in the angled section 116B.

Suitable sag sensors 220 may include any pressure sensor known to those skilled in the art, or any sensor that enables the computation of density or direct measurement of density in a fluid. For example, the sag sensors 220 may include, but are not limited to, sensors using infrared density-measurement methods, sensors using direct-density measurement methods, and sensors using vibratory density-measurement methods.

In certain embodiments, the sag sensor 220 may be a sensor configured to measure or detect a physical property or characteristic of the drilling fluid 126 disposed within the bore hole 116, for example viscosity, conductivity, magnetic field strength, optical transparency, absorptivity of electromagnetic radiation, etc. This property may have a known correlation with density for the particular composition of the drilling fluid 126 and, therefore, the density of the drilling fluid 126 can be determined based on measurement of the physical property or characteristic. While the disclosure is presented in terms of sensors that directly measure pressure, any sensor that measures or detects one or more physical properties or characteristics of a fluid may be substituted in place of the sag sensors 220 without departing from the scope of this disclosure.

In other embodiments, the sag sensor 220 may be an optical computing device that employs an integrated computational element (ICE), also known as a multivariate optical element (MOE). Such optical computing devices may be configured to receive an input of electromagnetic radiation from the drilling fluid 126, and produce an output of electromagnetic radiation from an ICE element arranged therein. The electromagnetic radiation that optically interacts with the ICE element is changed so as to be readable by a detector, such that an output of the detector can be correlated to at least one characteristic of the drilling fluid 126 being measured or monitored. The output of electromagnetic radiation from the ICE element can be reflected electromagnetic radiation, transmitted electromagnetic radiation, and/or dispersed electromagnetic radiation.

Whether reflected or transmitted electromagnetic radiation is analyzed by the detector may be dictated by the structural parameters of the optical computing device as well as other considerations known to those skilled in the art. In addition, emission and/or scattering of the drilling fluid 126, for example via fluorescence, luminescence, Raman scattering, and/or Raleigh scattering, can also be monitored by such optical computing devices. In some embodiments, suitable structural components for the exemplary optical computing devices are described in commonly owned U.S. Pat. Nos. 6,198,531; 6,529,276; 7,123,844; 7,834,999; 7,911,605; 7,920,258; 8,049,881; and 8,208,147, and U.S. patent application Ser. Nos. 12/094,465 and 13/456,467, each of which is incorporated herein by reference in its entirety.

In some embodiments, the sag sensor 220 may be an optical computing device including an ICE element configured to detect or otherwise measure the spectral fingerprint of a particular weighting material, such as barite, and thereby determine the concentration of the weighting material within the drilling fluid 126. In other embodiments, the sag sensor 220 may be an optical computing device including an ICE element configured to detect or otherwise measure the spectral fingerprint of a base oil in an oil-based drilling fluid 126. A change in the concentration of the weighting material will cause a corresponding change in the concentration of the base oil, and it may be more desirable to measure the concentration of the base oil than the weighting material. For example, there may be multiple materials suspended in the drilling fluid and measurement of the concentration of the base oil may replace multiple individual measurements of the various concentrations of the multiple suspended materials. In yet other embodiments, the sag sensor 220 may be an optical computing device including an ICE configured to detect or otherwise measure the spectral fingerprint of water, as measuring the concentration of water in a water-based drilling fluid 126 may be desirable for the same reasons as discussed above with regard to an oil-based drilling fluid 126.

A spectral fingerprint is an intensity versus frequency pattern of light that is received from the substance being examined, wherein a material will have a particular pattern that is referred to as the "spectral fingerprint" of that material as detection of that pattern is indicative of the presence of that material. In a brief and simplified summary, a spectral fingerprint of the drilling fluid 126 can be developed by separating light coming from the drilling fluid 126, e.g. light coming from a source and reflected by the drilling fluid 126, can be measured at a plurality of different frequencies. Each component of the drilling fluid 126 will contribute to the relative intensities at the plurality of frequencies according to the percentage amount of that component in the drilling fluid 126, and therefore the amount of the component can be derived from the combined spectral fingerprint of the drilling fluid 126. Once the amount of each component of the drilling fluid 126 is known, a total density of the measured drilling fluid 126 can be calculated.

While sag is, in actuality, the formation of a density gradient within the borehole 116 as the weighting material settles, sag may be more easily detected by measuring the pressures at various points within the portion of the borehole in which settling is occurring. Pressure can be considered an indirect indication of settling, as the pressure at any specific point is dependent upon the density of the fluids above that point and the settling of weighting material from above the point to below the point will cause a change in pressure as the settling progresses. While the local density of the drilling fluid 126 is the direct physical property of interest, the density may be measured either directly or calculated indirectly, for example by measurement of the concentration of one or more components of the drilling fluid 126 and calculation of the density based on known densities of the components, or measurement of the pressure within the borehole 116 and calculation of the density based on a sag model using the actual borehole 116 and drilling fluid 126.

Figure 5:
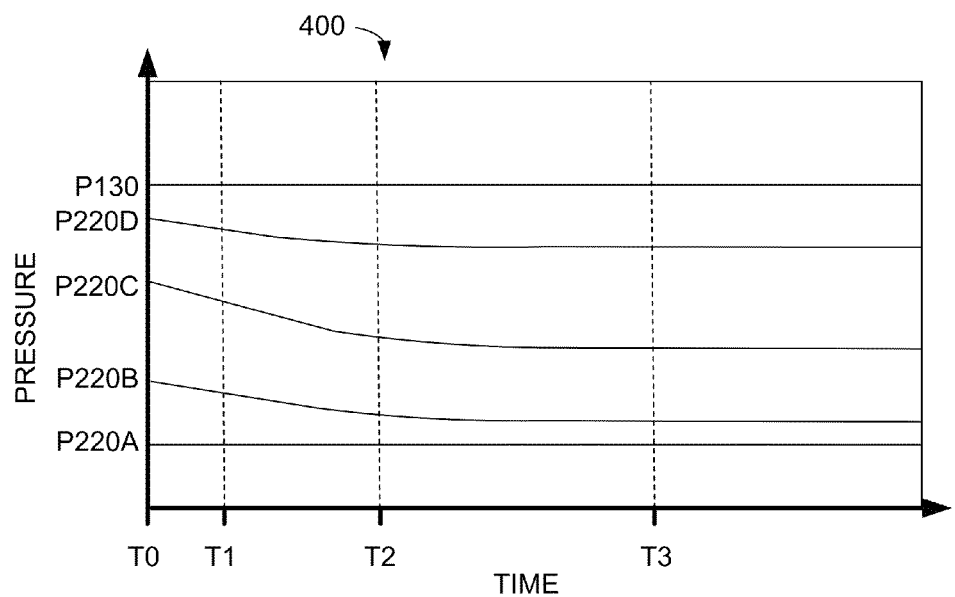
FIG. 5 is a qualitative plot of pressures at the various sensor locations of FIG. 4 during a sag event, according to one or more embodiments.
Figure 6:
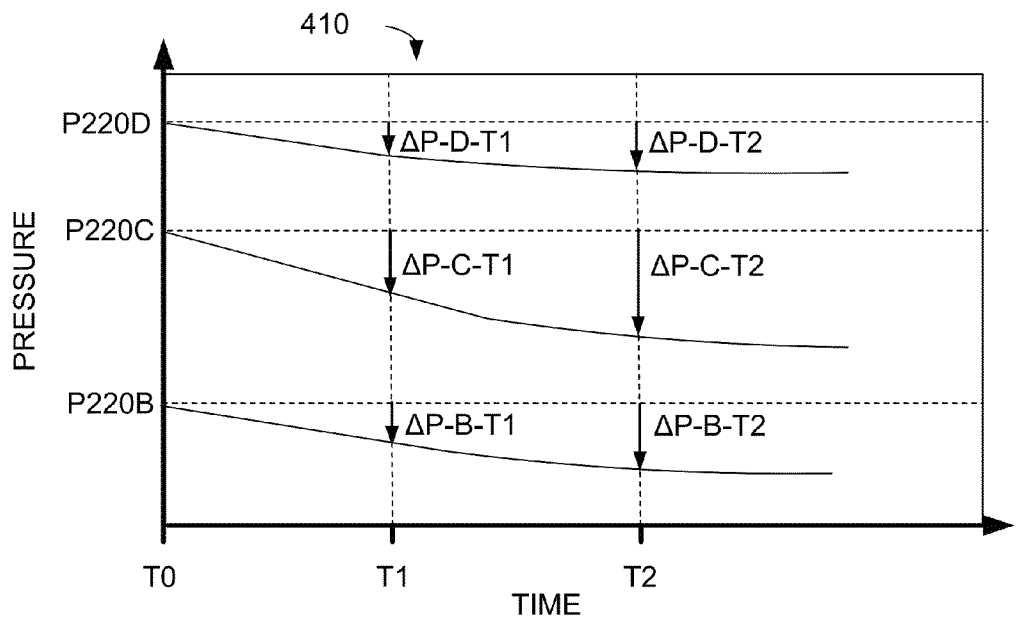
FIGS. 6 and 7 illustrate exemplary methods of evaluating pressures at the distributed sensors of FIG. 4, according to one or more embodiments.
Figure 7:
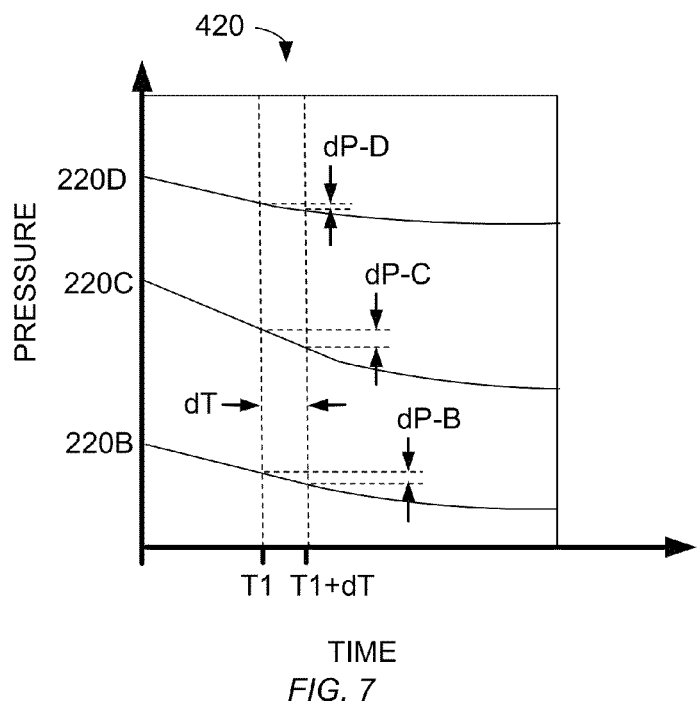

FIGS. 5-7 qualitatively discuss the results of repeated pressure measurements taken at various points along a borehole 116 and the amount of sag that is indicated by the pressure measurements. While the use of a sag model is not directly discussed, the amount of sag is determined from pressure measurements using such a model for, in this example, the borehole 116 and sensors 130 and 220A-220D shown in FIG. 4. While sag may be considered, for a strict interpretation of "sag," to start immediately upon cessation of circulation, a "sag event" is typically considered to be an amount of sag that has progressed sufficient to potentially present a problem of some sort. Moreover, sag is typically evaluated for as an overall condition and not at single points within the borehole 116. In certain embodiments, e.g. with the use of a complete computer model that includes the dimensions and features of the borehole 116 and composition and characteristics of the drilling fluid 126, a series of pressure measurements taken by single pressure sensor, e.g. sag sensor 220C, within a region in which sag is occurring, e.g. the angled borehole portion 116B, may be sufficient to determine the overall amount of sag that is occurring over time and identify or, in certain embodiments, predict the point in time at which a problematic amount of sag, i.e. severe sag, has occurred or will occur.

Referring now to FIG. 5, with continued reference to FIG. 4, illustrated is a qualitative plot of pressures at the various sensor locations 130, 220A-D during a sag event, according to one or more embodiments. Time T0 represents the time of cessation of circulation of the drilling fluid 126 within the borehole 116 and the pressures P130, P220A, P220B, P220C, and P220D at T0 represent the initial static pressures at the locations of the respective sensors 130 and 220A-220D. The curves shown in FIG. 5 are illustrative in nature and are not intended to represent actual pressures of a particular well unless otherwise stated. If a sag event does not occur, then the pressures P130, P220A-D would remain almost constant while the drilling fluid is quiescent except for thermal variations in the borehole 116 and the resultant minor pressure variations.

The PWD sensor 130 is generally not able to detect sag. Even in the presence of sag, the pressure P130 at the location of the PWD sensor 130 may remain relatively constant over time, as the total weight of the drilling fluid 126 above the PWD sensor 130 remains constant although the weighting materials may settle within the section 116B of the borehole 116. The problem with the PWD sensor 130 is that the hydrostatic pressure in the drilling fluid 126 is being measured in the wrong place to accurately detect a sag event. According to the present disclosure, distributing a plurality of sensors, such as sensors 220A-D, along the drill string 108 can provide near-real-time detection of a sag event so as to allow the timely implementation of mitigation methods.

The hydrostatic pressure P220A at the location of sag sensor 220A, which is disposed within the vertical section 116A, may also remain relatively constant over the time period of interest shown in FIG. 5. While sag will eventually occur in the vertical section 116A, it is the accelerated sag that occurs in the angled section 116B due to the boycott effect, discussed above, that presents the greater concern. Severe sag, i.e., sag that is sufficient to create a pressure spike or drag problems for the drill string 108, may develop in the angled section 116B long before the same problem manifests itself in the vertical section 116A, and so the time period of interest in FIG. 5 is sufficiently shortened that the amount of sag that occurs in the vertical section 116A is not significant.

The pressures at the locations of the three sag sensors 220B, 220C, and 220D plotted as pressures P220B, P220C, and P220D, respectively, in FIG. 5, that are distributed through the angled section 116B, may gradually decrease as the weighting material settles below each of the respective sensors 220B-220C. As the mechanisms of settling, even in the presence of the boycott effect, are generally understood, a simulation or computer model may be constructed that may predict the pressure at any location within the borehole 116 and at any time for a given amount of sag. For a particular well that is circulating a particular drilling fluid 126, theoretical hydrostatic pressures in the wellbore 116 can be calculated and compared to the pressures measured by each distributed sag sensor 220A-D. By comparing the theoretical pressures to the measured pressures at each sag sensor 220A-D, the sag rate, i.e. density-change rate, for various annular sections of the borehole 116 can be calculated or otherwise determined.

Referring to FIGS. 6 and 7, with continued reference to FIG. 4, illustrated are exemplary methods of evaluating pressures at the distributed sensors 220B-D, according to one or more embodiments. FIG. 6 depicts the theoretical pressures P220B, P220C, and P220D, recorded at the three sag sensors 220B, 220C, and 220D, as dashed lines. The measured pressures are represented as the solid lines. In FIG. 6, the characteristic of interest is the total pressure drop from the baseline pressure that was measured at time T0 and indicated in FIG. 6 as the horizontal dashed lines at P220B, P220C, and P220D. The total pressure drop at each time T1, T2, etc. is indicated by the vertical arrow, for example the arrow labeled "ΔP–D–T1" is the pressure drop from baseline at sag sensor 220D at time T1. By calculating the pressure drops ΔP–D–T1, ΔP–C–T1, etc. at times T1, T2, etc. during a sag event, the severity of the sag event can be determined and, if warranted, remediation actions may then be undertaken. In one or more embodiments, an average density change may be computed using the model of the borehole 116 and drilling fluid 126 and the average compared to one or more thresholds to determine whether sag has occurred or whether the sag is severe enough to warrant corrective action. In one or more embodiments, the local density changes at the three sag sensors 220B, 220C, and 220D may be computed using the model of the borehole 116 and individually compared to one or more thresholds to determine whether sag has occurred or whether the sag is severe.

FIG. 7 is another embodiment of a method of determining whether sag has occurred and estimating the severity of the sag using the slope of the measured pressure. In one or more embodiments, a differential pressure drop dP-D for sensor 220D, and similar differential pressure drops for the pressures measured at other sensors 220C, 220D, may be determined from pressures P220–T1 and P220–T1+dT measured at a first time T1 and a second time T1+dT. From the differential pressure drop dP-D (P220–T1+dT–P220–T1) and the differential time dT (T1+dT–T1), an instantaneous measured slope of the pressure curve P220D can be determined. Similarly, the measured slope of pressures curves P220B and P220C may be determined. In one or more embodiments, a theoretical instantaneous slope of pressure curves P220B, P220C, and P220D may be computed using the model of the borehole 116. In one or more embodiments, one or more of the measured slopes and the theoretical slopes may be individually compared to one or more thresholds to determine whether sag has occurred or whether the sag is severe. In one or more embodiments, the terms dP/dt for each of the pressure curves P220B, P220C, and P220D may be combined with the model to calculate a single average differential density dDen/dt and compared to one or more thresholds to determine whether sag has occurred or whether the sag is severe. It will be apparent to those of skill in the art that the measured and theoretical slopes may be compared to each other or combined with the sag model and then compared to a threshold in other ways without departing from the scope of this disclosure.

Figure 8:
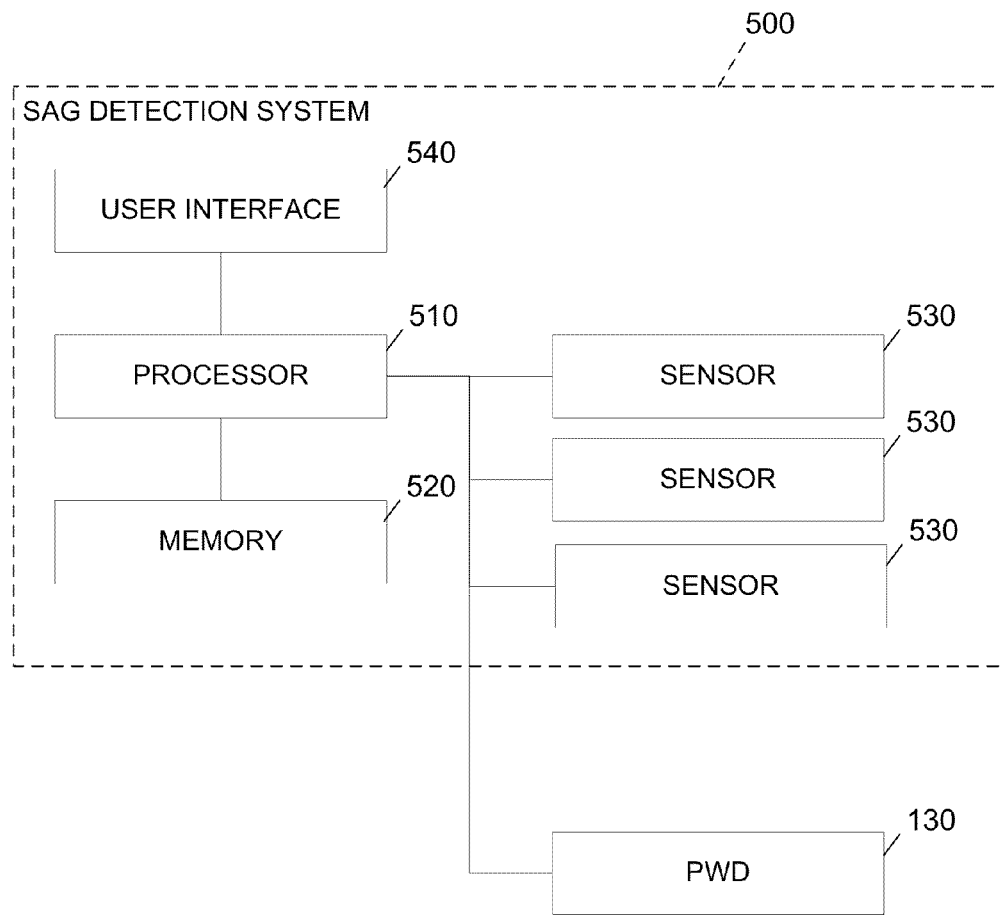
FIG. 8 is a block diagram of an embodiment of a sag detection system, according to one or more embodiments.

FIG. 8 is a block diagram of an embodiment of an exemplary sag detection system 500, according to one or more embodiments. The system 500 may include one or more sensors 530 used to detect or otherwise measure pressure of a drilling fluid 126 within the borehole 116. In one or more embodiments, the sensors 530 may be similar to one or more of the sensors 220A-D of FIG. 4. The sensors 530 may be communicatively connected to a processor 510 which may communicate with a non-volatile memory 520. The processor 510 may be configured to receive pressure measurements from the sensors 530 and process the measurements according to instructions retrieved from the memory 520.

In certain embodiments, the memory 520 may contain a computer model adapted to predict pressures at various points in a borehole 116 based on at least one of a borehole dimension and a characteristic of the drilling fluid 126 disposed within the borehole 116. In certain embodiments, the processor 510 may predict a pressure at a certain point in the borehole 116 at least partially based on the model and compare the predicted pressure to a measured pressure. In certain embodiments, the processor 510 may then communicate the results to a user for consideration.

In some embodiments, the processor 510 may be configured to transmit the results (either wired or wirelessly) to a user interface 540 configured to display the results of the comparison such that the operator may make an informed decision as to the status of the borehole 116. In one or more embodiments, the processor 510 may provide alerts or alarms through the user interface 540 based at least partially on the comparison. The alerts or alarms may warn the operator of the onset of a sag event. In one or more embodiments, the user interface 540 may contain one or more of a display screen (e.g., a graphical user interface, or the like), a printer, a network interface communicatively coupled to a remote system, an audio output device such as a speaker, a visual output device such as a flashing light, a pager, a cell phone, a radio, or other device adapted to communicate information to the operator. In one or more embodiments, the system 500 may be further configured to accept information from the PWD sensor 130.

Figure 9:
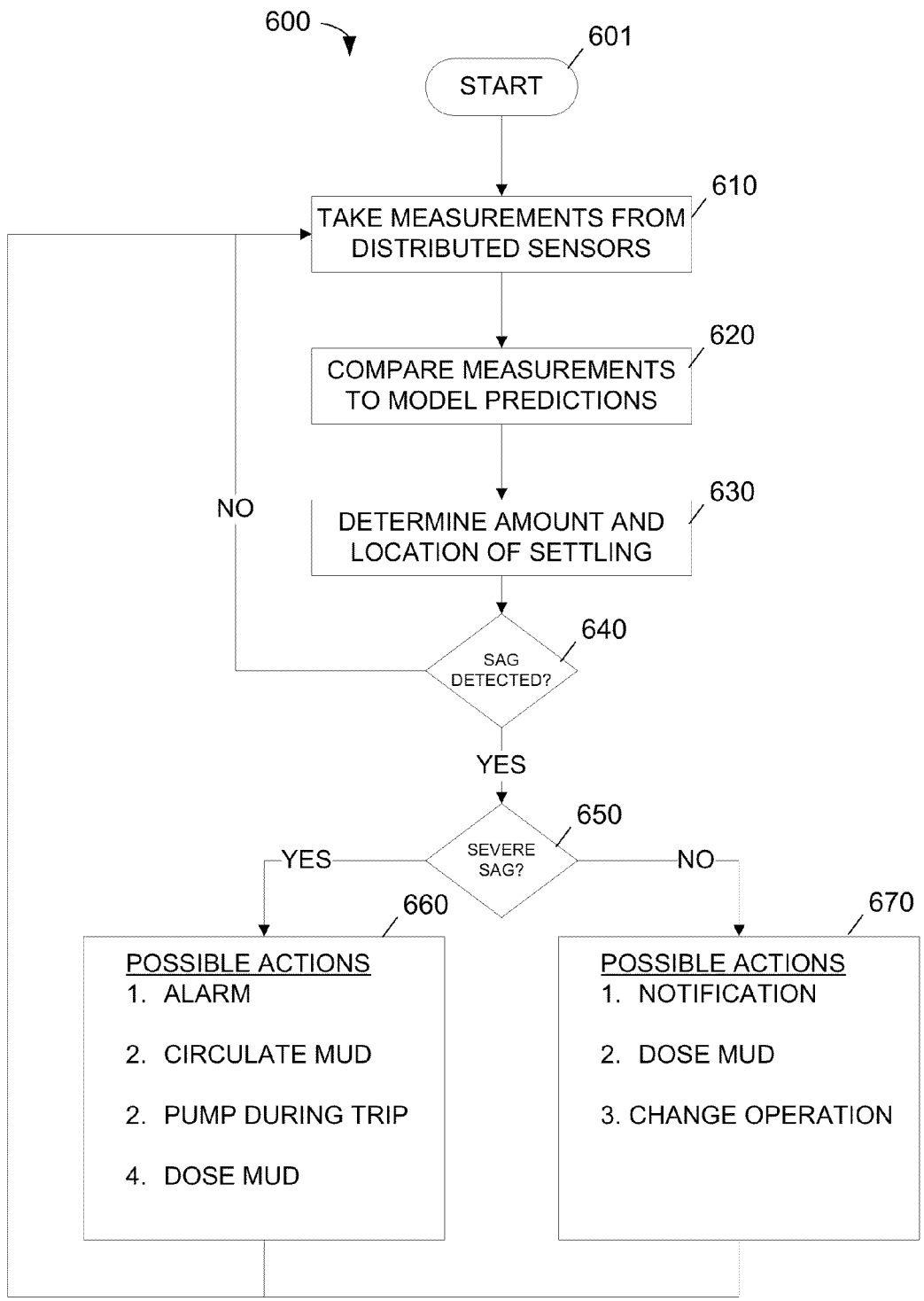
FIG. 9 is a flow diagram of an exemplary method of detecting and responding to the detection of a sag event, according to one or more embodiments.

FIG. 9 is a flow diagram 600 of an exemplary method 600 of detecting and responding to the onset of a sag event, according to one or more embodiments. Starting at the START 601, the method 600 obtains measurements from one or more sag sensors 220 that may be distributed along the drill string 108, as at 610. A sag model may then be employed to predict pressures at the locations of the sag sensors 220 and the measured pressures are compared to the predicted pressures using, for example, one of the methods shown in FIGS. 6 and 7, as at 620. The amount of settling that has occurred is then determined, as reflected in a change in density of the drilling fluid 126, and the location along the drill string 108 where the weighting material has settled, as at 630. The method 600 then proceeds to determine whether the settling constitutes sag, as at 640. In one or more embodiments, whether sag has indeed occurred may be determined through a comparison of a density or change in density to a predetermined threshold or model. If the determined amount of settling does not constitute problematic sag, then the method 600 returns to 610 to obtain additional pressure measurements from the sensors.

If it is determined that sag is detected, however, the method 600 then proceeds to determine whether the sag is severe, as at 650. In one or more embodiments, whether the sag event is severe may be determined through a comparison of a density or change in density to a threshold. If the sag is determined to be severe, the method 600 may proceed via a first algorithm to provide several possible actions to pursue, as at 660. Possible actions include, but are not limited to, an alarm, starting the pump 120 in order to circulate the drilling fluid 126, pumping while tripping, e.g. pulling the drill string 108 from the borehole 116 so as to replace a drill bit 114, adding a modifier in the form of a dose mud to the drilling fluid 126, or other actions as described or combinations of several actions above with respect to FIG. 3.

If the sag is determine to not be severe, the method 600 may proceed via a second algorithm to provide several other possible actions to pursue, as at 670. Possible actions include, but are not limited to, notifying the operator of the onset of a sag event within the borehole 116, adding a modifier in the form of a dose mud to the drilling fluid 126, modifying the current operation of the drill rig 100, or other actions as described above with respect to FIG. 3. After the first or second algorithms have completed the action selected in response to the detected sag, the method 600 may return to start a new cycle of measurement and analysis, as at 610. In one or more embodiments, this cycle continues until drilling operations are concluded and the drilling fluid 126 is completely circulated out of the borehole 116.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method of detecting sag in a drilling fluid within a borehole, the method comprising:
   (A) measuring a first pressure with a first sensor positioned at a point within the borehole, the first pressure being measured at a first time following cessation of a flow of the drilling fluid within the borehole;
   (B) measuring a second pressure with the first sensor at the point within the borehole and at a second time following cessation of the flow of the drilling fluid;
   (C) determining a first theoretical pressure and a second theoretical pressure at the first and second times, respectively, at the point based on a computer model that includes known dimensions and features of the borehole at the point and a current composition of the drilling fluid;
   (D) calculating a theoretical pressure slope between the first theoretical pressure and the second theoretical pressure;
   (E) receiving the first and second pressures with a processor communicatively coupled to the first sensor and calculating a pressure drop based on the first and second pressures; and
   (F) comparing the pressure drop and the theoretical pressure slope using the processor to a threshold indicating sag such that:
   when the pressure drop and the theoretical pressure slope does not exceed the threshold indicating sag, repeating the (A)-(F) steps until the threshold indicating sag is exceeded; and
   when the pressure drop and the theoretical pressure slope exceed the threshold indicating sag, undertaking at least one corrective action selected from the group consisting of adding a modifier to the drilling fluid, changing a rate of rotation of a drill string, restarting flow of the drilling fluid, pumping the drilling fluid while moving the drill string, and any combination thereof.

2. The method of claim 1, wherein the point is above a bottom of the borehole.

3. The method of claim 1, wherein determining the first and second theoretical pressures of the drilling fluid further comprises using at least one of a density of the drilling fluid, a rheological measurement of the drilling fluid and flow characteristics of the drilling fluid.

4. The method of claim 1, wherein determining the first and second theoretical pressures further comprises using information regarding at least one of a diameter of the borehole, an angle of a portion of the borehole, a length of an angled portion of the borehole, and an outer diameter of a drill string.

5. The method of claim 1, wherein the first theoretical pressure comprises a hydrostatic pressure.

6. The method of claim 1, wherein the threshold is calculated based at least in part on a time interval from the cessation of flow of the drilling fluid to the first time.

7. A system for detecting sag in a drilling fluid within a borehole, comprising:
   at least one sensor positioned within the borehole at a point to monitor the drilling fluid at the point and thereby (A) obtain a first pressure of the drilling fluid at a first time following cessation of a flow of the drilling fluid within the borehole and a second pressure of the drilling fluid at a second time following cessation of the flow of the drilling fluid; and
   a processor communicatively coupled to the at least one sensor for receiving the first and second pressures, the processor being programmed to (B) calculate a pressure drop based on the first and second pressures and (C) determine a first theoretical pressure and a second theoretical pressure at the first and second times, respectively, at the point based on a computer model that includes known dimensions and features of the borehole at the point and a current composition of the drilling fluid,
   wherein the processor is further programmed to (D) calculate a theoretical Pressure slope between the first theoretical pressure and the second theoretical pressure and (E) compare the pressure drop and the theoretical pressure slope to a threshold indicating sag, and programmed to either (1) repeat (A)-(E) until the threshold indicating sag is exceeded by the pressure drop and the theoretical pressure slope or (2) initiate at least one corrective action selected from the group consisting of adding a modifier to the drilling fluid, changing a rate of rotation of a drill string, restarting flow of the drilling fluid, pumping the drilling fluid while moving the drill string, and any combination thereof when the threshold indicating sag is exceeded by the pressure drop and the theoretical pressure slope.

8. The system of claim 7, wherein the at least one sensor is position at a point above a bottom of the borehole.

9. The system of claim 7, wherein the at least one sensor is coupled to a drillstring extended within the borehole.

10. The system of claim 7, wherein the at least one sensor comprises a plurality of sensors distributed at a respective plurality of points along the borehole and communicatively coupled to the processor, each sensor monitoring the drilling fluid at the first time and thereby providing corresponding pressures to the processor.

11. The system of claim 7, wherein the processor is programmed to determine the first and second theoretical pressures of the drilling fluid using at least one of a density of the drilling fluid, a rheological measurement of the drilling fluid and flow characteristics of the drilling fluid.

12. The system of claim 7, wherein the processor is programmed to determine the first and second theoretical pressures of the drilling fluid using at least one of a diameter of the borehole, an angle of a portion of the borehole, a length of an angled portion of the borehole, and an outer diameter of a drill string extended within the borehole.

13. The system of claim 7, wherein the first theoretical pressure comprises a hydrostatic pressure.

14. The system of claim 7, wherein the threshold is calculated based at least in part on a time interval from the cessation of flow of the drilling fluid to the first time.

* * * * *